United States Patent [19]
Poindexter et al.

[11] Patent Number: 6,001,836
[45] Date of Patent: Dec. 14, 1999

[54] DIHYDROPYRIDINE NPY ANTAGONISTS: CYANOGUANIDINE DERIVATIVES

[75] Inventors: Graham S. Poindexter, Old Saybrook; R. Thomas Swann, Hamden; Marc A. Bruce, Wallingford; Mendi A. Morton, Middletown; Yazhong Huang, Wallingford; Sing-Yuen Sit, Meriden, all of Conn.; James Guy Breitenbucher, Richmond, Calif.

[73] Assignee: Bristol-Myers Squibb Company, Princeton, N.J.

[21] Appl. No.: 09/084,692

[22] Filed: May 26, 1998

Related U.S. Application Data

[60] Provisional application No. 60/047,990, May 28, 1997.

[51] Int. Cl.$^6$ .................. C07D 401/10; A61K 31/445
[52] U.S. Cl. .................. 514/255; 514/318; 514/332; 514/356; 546/194; 546/263; 546/321; 544/365
[58] Field of Search .................. 546/321, 194, 546/263; 544/365; 514/356, 318, 332, 255

[56] References Cited

U.S. PATENT DOCUMENTS

| | | | |
|---|---|---|---|
| 4,829,076 | 5/1989 | Szilagyi et al. | 546/321 |
| 5,554,621 | 9/1996 | Poindexter et al. | 514/278 |
| 5,635,503 | 6/1997 | Poindexter et al. | 514/218 |
| 5,668,151 | 9/1997 | Poindexter et al. | 514/318 |

OTHER PUBLICATIONS

David Alker, et al., "Long–Acting Dihydropyridine Calcium Antagonists. 4. Synthesis and Structure–Activity Relationships for a Series of Basic and Nonbasic Derivatives of 2-[(2–Aminoethoxy)methyl]–1,4–dihydropyridine Calcium Antagonists," *J. Med. Chem.*, 1990, 33, 585–591.

*Primary Examiner*—Jane Fan
*Attorney, Agent, or Firm*—Richard P. Ryan

[57] ABSTRACT

A series of non-peptidergic antagonists of NPY have been synthesized and are comprised of cyanoguanidine derivatives of 4-phenyl-1,4-dihydropyridines of Formula (I).

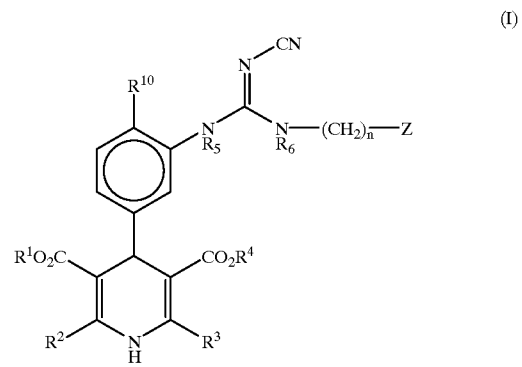

As antagonists of NPY-induced feeding behavior, these compounds are expected to act as effective anorexiant agents in promoting weight loss and treating eating disorders.

8 Claims, No Drawings

DIHYDROPYRIDINE NPY ANTAGONISTS: CYANOGUANIDINE DERIVATIVES

CROSS REFERENCE TO RELATED APPLICATION

This non-provisional application claims the benefit of U.S. provisional application 60/047,990 filed May 28, 1997.

BACKGROUND OF THE INVENTION

The present invention concerns heterocyclic carbon compounds comprising 4-phenyl-1,4-dihydropyridines having various aminoalkyl moieties connected via a cyanoguanidine group to the 3-position of the 4-phenyl ring. These compounds are NPY antagonists.

A substantial body of art has accumulated over the past two decades with respect to the 4-aryl-1,4-dihydropyridine class of compounds. Syntheses of compounds in this category have been driven by their pharmacologic actions involving calcium channels rendering them useful for treating cardiovascular disorders such as ischemia and hypertension.

U.S. Pat. No. 4,829,076 to Szilagyi, et al. is an example of such substituted dihydropyridine derivatives, disclosing and claiming inter alia compounds of formula (1) as calcium antagonists for treating hypertension.

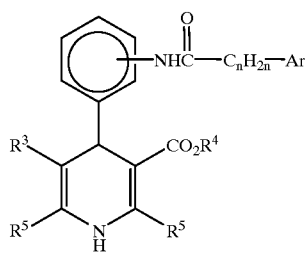

(1)

The closest art would be our previous work involving 4-(3-substituted-phenyl)-1,4-dihydropyridine derivatives having NPY antagonist properties. These derivatives conform to structural formula

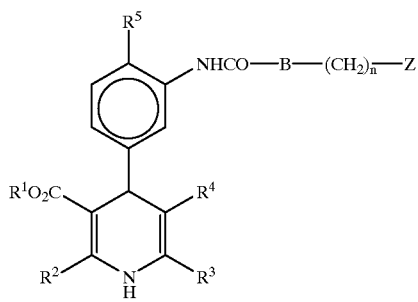

(2)

In (2) B is either a covalent bond or the group —NH—. The symbol Z denotes hetaryl moieties, examples being piperidine or piperazine.

In U.S. Pat. No. 5,554,621, Z is a fused ring or spiro-fused nitrogen heterocycle. In U.S. Ser. No. 482,355, Z is a piperazinyl or homopiperazinyl moiety. Z is a piperidinyl or tetrahydropyridinyl moiety in U.S. Ser. No. 639,968.

These reference compounds are easily distinguished from the compounds of the instant invention by virtue of the linking functional groups. The cyanoguanidine linking moiety is a novel structural feature in the new compounds, connecting the side-chain to the 4-phenyl ring. A cyanoguanidine moiety has previously appeared in a different location in 4-phenyl-1,4-dihydropyridine derivatives.

Alker, et al. in *J. Med. Chem.*, 1990, 33, 585–591 disclosed, inter alia, compounds of formula (3) having calcium antagonism activity.

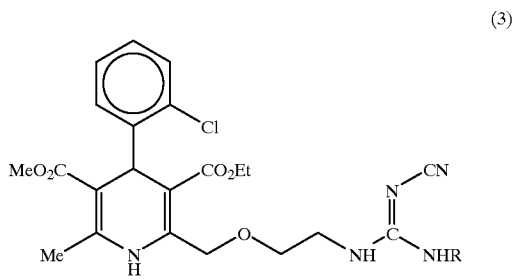

(3)

As can be seen, these compounds differ structurally from the compounds of the present invention.

In summary, the prior art does not disclose nor suggest the unique combination of structural fragments which embody these novel dihydropyridine derivatives which possess good antagonist activity at NPY $Y_1$ receptor sites while having reduced cardiovascular effects.

SUMMARY AND DETAILED DESCRIPTION OF THE INVENTION

The present invention comprises compounds of Formula (I), their

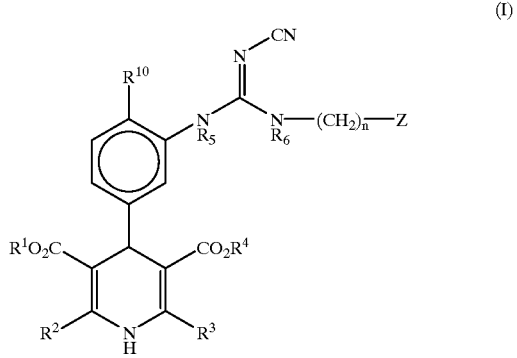

(I)

pharmaceutically acceptable acid addition salts and/or their hydrates thereof. In the foregoing structural Formula (I), the symbols $R^1$–$R^6$, $R^{10}$, n and Z have the following meanings.

$R^1$ to $R^4$ are independently selected from lower alkyl;

$R^5$ and $R^6$ are independently selected from hydrogen and lower alkyl;

n is an integer selected from 2 to 5;

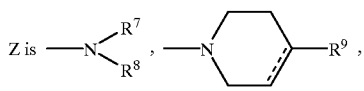

Z is

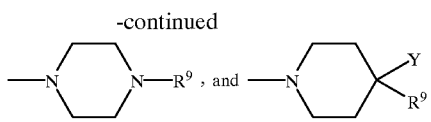

in which $R^7$ and $R^8$ are independently selected from lower alkyl and lower alkanol; the solid and broken line denote a single or double covalent bond; $R^9$ is selected from hydrogen; lower alkyl; —$CO_2R^1$; —$(CH_2)_mX$ and —$(CH_2)_n$—$NR^{11}R^{12}$, wherein m is zero or an integer from 1 to 3 and X is $C_{3-7}$ cycloalkyl, naphthyl, and

$R^{13}$ can be lower alkyl, lower alkenyl, lower alkoxy, hydrogen, halogen, hydroxy and dialkylamino. $R^{11}$ and $R^{12}$ are each lower alkyl or are taken together as a $C_{3-5}$ alkylene chain or an ethyl-oxy-ethyl chain;

Y is hydrogen, hydroxy, cyano, and —$CO_2Me$;

$R^{10}$ is hydrogen or halogen.

The term "lower" refers to substituents such as alkyl or alkoxy that contain from one to four carbon atoms; and to alkenyl groups containing from two to four carbon atoms. $R^{11}$ and $R^{12}$ are independently selected from lower alkyl to give tertiary amine groups, or $R^{11}$ and $R^{12}$ can be taken together as a propyl, butyl or pentyl chain, thereby giving a nitrogen-containing ring, or as an ethyl-oxy-ethyl chain, thereby giving a morpholinyl ring.

Preferred compounds are Formula (I) compounds wherein $R^1$–$R^4$ are methyl, $R^5$ and $R^6$ are hydrogen, Z is piperidine and $R^9$ is selected from phenyl, naphthyl and cycloalkyl.

The compounds of the present invention can exist as optical isomers and both the racemic mixtures of these isomers as well as the individual optical isomers themselves are within the scope of the present invention. The racemic mixtures can be separated into their individual isomers through well-known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, dichloroacetic acid, tartaric acid, lactic acid, succinic acid, citric acid, maleic acid, fumaric acid, sorbic acid, aconitic acid, salicyclic acid, phthalic acid, enanthic acid, and the like.

The Formula (I) compounds can be produced by utilizing the following processes. The range of Formula (I) compounds are obtained by selecting the appropriate starting materials for use in these processes. General processes for synthesis of Formula (I) compounds are shown in Schemes 1 and 2. The symbols $R^1$–$R^{10}$, n and Z are as previously defined. The symbol R is lower alkyl.

Nearly all desired Formula (I) products can be synthetically derived from aniline intermediate of Formula (IV) and various Formula (V) intermediates. As shown in pathway A of Scheme 1, the aniline compound (IV) is converted to the isothiocyanate (III) by use of thiocarbonyldiimidazole. Treatment of (III) with sodium cyanamide results in the sodium N-cyanoisothiourea salt (II) which can be reacted with various amines (V) to produce the Formula (I) products. An alternative approach is shown in pathway B wherein the isothiocyanate intermediate (III) is converted to the thiourea compound (X) which is converted to the carbodiimide compound (XI) using phosgene. Addition of sodium cyanamide provides the product (I).

Scheme 2 is used for synthesis of Formula (I) products in which $R^5$ is lower alkyl. The aniline intermediate (IV) is acylated using trifluoroacetic anhydride to give compound (VI) which is alkylated with an alkyl iodide, after nitrogen anion formulation with sodium hydride, to provide the monoalkylated aniline intermediate (XIV) following basic hydrolysis of (VII). Reaction of (XIV) with the sodium N-cyanoisothiourea compound (IX) in the presence of $HgCl_2$ yields the Formula (I) product wherein $R^5$ is alkyl.

The Formula (IX) intermediate can be obtained from compound (V) by first treating with thiocarbonyldiimidazole and then with sodium cyanamide.

Formula (IV) intermediates are readily available via variations of the Hantzsch synthetic reaction applied to appropriate starting materials such as the nitrobenzaldehyde (VIII).

Scheme 3

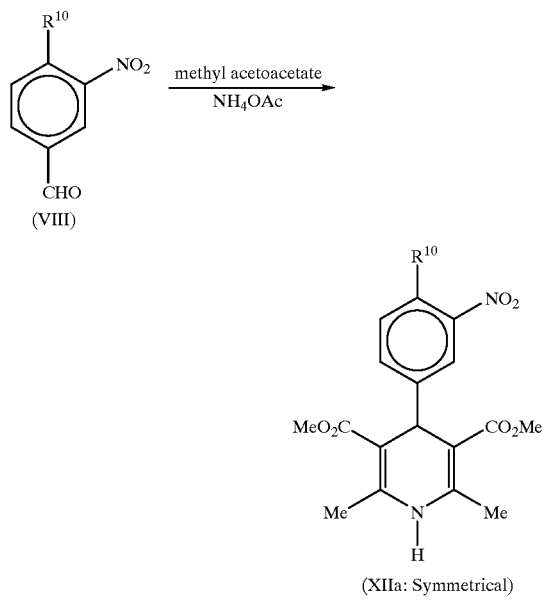

As seen in Scheme 3, (XIIa) is a symmetrical dihydropyridine compound. Unsymmetrical dihydropyridines, e.g. where $R^1 \approx R^4$ and/or $R^2 \approx R^3$, are readily prepared as in Scheme 4, using modified Hantzsch conditions starting with Knoevenagel adducts and appropriate amino crotonates.

Scheme 4

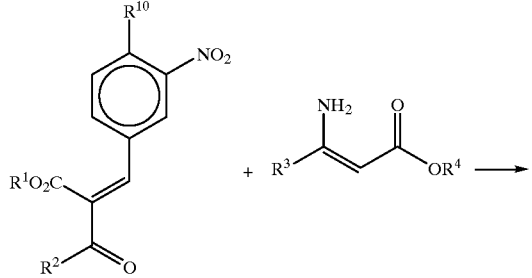

-continued

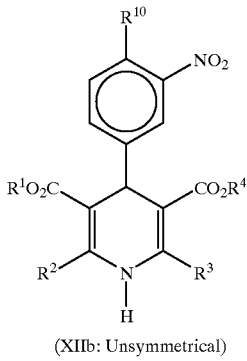

(XIIb: Unsymmetrical)

A number of these starting materials and intermediate dihydropyridines are commercially available and/or described in the literature. Use of the Hantzsch reaction and its modifications would be known to one skilled in the synthetic chemical arts.

Reduction of nitrophenyldihydropyridines, e.g. (XII), using any of several standard reduction processes provides the starting Formula (IV) aniline intermediates used in the present invention.

Additional reaction intermediates and Formula (I) products can be prepared by appropriate modification of the foregoing synthetic schemes and procedures. Additional examples and experimental procedures are provided infra.

The compounds of this invention demonstrate binding affinity at NPY $Y_1$ receptors. This pharmacologic activity is assayed in SK-N-MC (human neuroblastoma) cell membranes using iodine-125-labeled I-PYY as a radioligand. The compounds of this invention had good binding affinities as evidenced by $IC_{50}$ values being about 10 µM or less at NPY $Y_1$ receptors. Preferred compounds have $IC_{50}$ values less than 100 nM and most preferred compounds have $IC_{50}$ values of less than 10 nM. Although as a class, these types of dihydropyridines have significant affinity for $\alpha_1$-adrenergic receptors and/or $Ca^{++}$ channels, the compounds of this invention possess much weaker affinities for $\alpha_1$ adrenergic receptors and $Ca^{++}$ channels. Pharmacologically, these compounds act as selective NPY antagonists at NPY $Y_1$ receptor sites. As such, the compounds of Formula (I) are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula (I) or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:
disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrythmia, peripheral vascular disease, and abnormal renal conditions such as impaired flow of fluid, abnormal mass transport, or renal failure;
conditions related to increased sympathetic nerve activity for example, during or after coronary artery surgery, and operations and surgery in the gastrointestinal track;
cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;
conditions related to pain or nociception;
diseases related to abnormal gastrointestinal motility and secretion, such as different forms of ileus, urinary incontinence, and Crohn's disease;
abnormal drink and food intake disorders, such as obesity, anorexia, bulimia, and metabolic disorders;
diseases related to sexual dysfunction and reproductive disorders such as benign prostatic hyperplasia and male erectile dysfunction;
conditions or disorders associated with inflammation;
respiratory diseases, such as asthma and conditions related to asthma and bronchoconstriction;
diseases related to abnormal homone release, such as leutinizing hormone, growth hormone, insulin and prolactin;
sleep disturbance and diabetes.

There is evidence that NPY contributes to certain symptoms in these disorders: hypertension, eating disorders, and depression/anxiety; as well as circadian rhythms. Compounds of this invention are expected to be useful in treating these disorders as well as sleep disturbance and diabetes.

Selected compounds are tested further for their ability to block or stimulate NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a Formula (I) compound or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 50 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat the various diseases, conditions, and disorders listed supra.

Therapeutically, the instant compounds are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethelene glycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C when not specified.

The nuclear magnetic resonance ($^1$H and $^{13}$C NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), singlet (s), multiplet (m), doublet (d), triplet (t) doublet of doublets (dd), quartet (q) or pentuplet (p). Abbreviations employed are DMSO-$d_6$, (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were generally employed using potassium bromide (KBr) as diluent. The elemental analyses are reported as percent by weight. Melting points were obtained using a Thomas Hoover capillary apparatus and are uncorrected. Mass spectra (m/z; MH$^+$) and analytic HPLC (retention time and peak area %) data were obtained.

A. Preparation of Intermediates

1. Starting Dihydropyridines

EXAMPLE 1

General Procedure for the Preparation of Knoevenagel Adducts (Precursors to Asymmetric Dihydropyridines)

As a general method, a mixture of 300 mmol each of 3-nitrobenzaldehyde and the requisite β-keto ester was dissolved in 250 mL of toluene and piperidine (2.5 mL) and glacial HOAc (5 mL) were added. The solution was then allowed to reflux several h during which time the theoretical amount of H$_2$O was removed by a Dean-Stark trap. The toluene was then removed in vacuo and the resulting Knoevenagel products purified by flash chromatography (SiO$_2$: EtOAc/Hex) or crystallization.

EXAMPLE 2

General Method for the Preparation of Starting Dihydropyridines (XII)

For symmetrical dihydropyridines (XIIa) the requisite β-keto ester (126 mmol), a 3-nitrobenzaldehyde (63 mmol), and NH$_4$OAc (95 mmol) were refluxed for several h in 150 mL of EtOH or i-PrOH using standard Hantzsch conditions. The crude reaction mixture was cooled to ambient temperature and the volatiles removed in vacuo. The symmetrical dihydropyridines were crystallized from EtOH or i-PrOH. Generally, for the asymmetrical dihydropyridines (XIIb), a mixture of the requisite Knoevenagel adduct (70 mmol) and an alkyl 3-aminocrotonate (70 mmol) was refluxed in i-PrOH overnight (24 h). The volatiles were then removed in vacuo and the crude products recrystallized from EtOH.

2. Aniline Intermediates of Formula (IV)

EXAMPLE 3

General Reductive Procedures for the Conversion of the Nitroaryl Dihydropyridines to the Anilines (IV)

Catalytic Hydrogenation Method A

To a N$_2$ solution of the nitro aromatic dihydropyridine (10 mmol) in 80 mL of EtOH, was added 0.5–1.0 g of 5% Pt on sulfided carbon and the resulting suspension shaken on a Parr Hydrogenation apparatus at room temperature under 60 psi of H$_2$. After several h the reduction was usually complete as judged by theoretical H$_2$ consumption. The suspension was then filtered through Celite and the filtrate concentrated in vacuo to give the anilines (IV). These were then purified by recrystallization or flash chromatography in the indicated solvents. In some of the examples the crude aniline derivatives were converted to a salt form and then recrystallized.

Iron Method B

In a 250-mL three-necked flask equipped with mechanical stirrer and reflux condenser was added a solution of $NH_4Cl$ (64 mmol) in 50 mL of $H_2O$, iron powder (38 mg-atom, 325 mesh) and a solution of the nitro aromatic dihydropyridine (11 mmol) in 50 mL of MeOH. The resulting mixture was stirred at reflux for 6 h and then filtered through Celite and rinsed with copious amounts of MeOH. The filtrate was partially concentrated in vacuo to yield an aq suspension, which was extracted with $CH_2Cl_2$. The combined organic extracts were dried over $Na_2SO_4$, filtered, and the volatiles removed in vacuo to yield the crude anilines (IV). These were purified as above in the hydrogenation method.

3. Formula (V) Diamine Intermediates

EXAMPLE 4

4-(3-Methoxyphenyl)-1-piperidineethanamine

A mixture of bromoacetonitrile (0.70 mL, 10 mmol), 4-(3-methoxyphenyl)piperidine (1.74 g, 9.1 mmol) and $K_2CO_3$ (1.3 g) in MeCN was stirred at room temperature for 3 days. The reaction mixture was partitioned between $CH_2Cl_2$ and $H_2O$, and the organic extract was dried ($Na_2SO_4$). The solvent was then removed in vacuo to afford [4-(3-methoxyphenyl)-1-piperidinyl]acetonitrile as an amber oil (2.03 g, 97%): MS (DCl) m/z 231 (MH$^+$). Anal. Calcd. for $C_{14}H_{18}N_2O.0.5 H_2O$: C, 70.27; H, 8.00; N, 11.71. Found: C, 70.12; H, 7.67; N, 11.87.

A solution of the analyzed amber oil (1.90 g, 8.26 mmol) in MeOH (50 mL) containing 30% aq. $NH_3$ (10 mL) and Raney nickel was hydrogenated in a Parr apparatus at 50 psi for 2 h. The catalyst was removed by filtration over Celite, and the solvent was then removed in vacuo from the filtrate to yield the desired compound as a pale blue oil (1.11 g, 58%). This material was subsequently reacted without further purification or characterization.

EXAMPLE 5

N-Methyl-3-(4-phenyl-1-piperidinyl)propanamine

A solution of 4-phenylpiperidine (480 mg, 3.0 mmol) and acrylonitrile (0.27 mL, 4.0 mmol) in MeCN (20 mL) was refluxed for 2 h. Solvent was removed in vacuo to give 3-(4-phenyl-1-piperidinyl)proparenitrile as a colorless oil (520 mg, 86%): MS (DCl) m/z 215 (MH$^+$). This oil was catalytically reduced in 99% yield to 4-phenyl-1-piperidinepropanamine by using the procedure given in Example 4.

A solution of this propanamine intermediate (5.45 g, 25 mmol) in ethyl formate (75 mL) was refluxed overnight. Solvent was removed in vacuo and the residue was taken up in $CH_2Cl_2$ and chromatographed over silica ($CH_2Cl_2$:MeOH, 7:3) with vacuum filtration to give N-[3-(4-phenyl-1-piperidinyl)propyl]formamide (5.54 g, 90%). This material (5.5 g, 22 mmol) was dissolved in anhydrous THF (50 mL) containing $BH_3.Me_2S$ (2.0 M in THF, 33 mL, 66 mmol) and refluxed overnight. The reaction mixture was then cooled, and was gradually quenched with MeOH (100 mL), followed by 3N HCl (100 mL). The resulting solution was refluxed overnight, and the solvent was then reduced in vacuo (to approximately 50 mL). This solution was made basic by the gradual addition of 20% NaOH, and then was extracted with $CH_2Cl_2$. The organic extract was dried ($Na_2SO_4$), and the solvent was removed in vacuo. The residue was subjected to bulb-to-bulb vacuum distillation (Kugelrohr apparatus) to afford the title compound as a colorless oil (5.1 g, 100%). MS (DCl) m/z 233 (MH$^+$). $^1$H NMR (CDCl$_3$) δ 7.22 (m, 5H), 3.54 (s, 1H), 3.06 (m, 2H), 2.71 (m, 2H), 2.48 (m, 6H), 2.03 (m, 2H), 1.77 (m, 6H). Anal. Calcd. for $C_{15}H_{24}N_2.0.1 H_2O$: C, 76.94; H, 10.42; N, 11.96. Found: C, 77.16; H, 10.80; N, 11.67.

4. Formula (IX) Isothiourea Sodium Salt Intermediates

EXAMPLE 6

3-(4-phenyl-1-piperdinyl)propyl isothiocyanate

A solution of 4-phenyl-1-piperidinepropanamine (Example 5 intermediate) (3.2 g, 14.7 mmol) and 1,1'-thiocarbonyldiimidazole (2.8 g, 15.7 mmol) in MeCN (100 mL) was stirred for 2 h. The reaction mixture was chromatographed by vacuum filtration over silica (MeCN) to furnish 1-(3-isothiocyanatopropyl)-4-phenylpiperidine as an amber oil which crystallized upon standing (1.25 g, 33%). mp 50–55° C.; MS (ESI) m/z 261 (MH$^+$); IR (KBr) 2113 cm$^{-1}$. $^1$H NMR (CDCl$_3$) δ 7.23 (m, 5H), 3.63 (t, 2 H, J=6.3 Hz), 3.08 (m, 2H), 2.55 (t, 2H, J=7.2 Hz), 2.50 (m, 1H), 2.15 (m, 2H), 1.95 (t, 2H, J=6.9 Hz), 1.86 (m, 4H). Anal. Calcd. for $C_{15}H_{20}N_2S.0.5 C_2H_3N$: C, 66.28; H, 7.82; N, 12.08. Found: C, 66.68; H, 7.75; N, 12.22.

EXAMPLE 7

N-Cyano-N'-[3-(4-phenyl-1-piperidinyl)propyl] isothiourea sodium salt

Sodium ethoxide (1.1 M, prepared from 127 mg, 5.5 mmol sodium in 5.0 mL EtOH under a nitrogen atmosphere) was added to a solution of cyanamide (231 mg, 5.5 mmol) in 5.0 mL EtOH. To an aliquot (1.0 mL, 0.55 mmol) of this 0.55 M solution was added dropwise a solution of 1-(3-isothiocyanatopropyl)-4-phenylpiperidine (120 mg, 0.55 mmol) in EtOH (5 mL). The mixture was briefly brought to a boil, and then was stirred at room temperature for 1 h. The solvent was removed in vacuo, and the residue was triturated in $Et_2O$ and filtered to give the compound as a fine white solid (140 mg, 79%).

5. Scheme 1 Intermediates (II, III)

EXAMPLE 8

1.4-Dihydro-4-[3-(isothiocyanato]phenyl)-2,6-dimethyl-3,5-pyridinedicarboxylic acid, dimethyl ester, hemihydrate (III)

1,4-Dihydro-4-(3-aminophenyl)-2,6-dimethyl-3,5-pyridinedicarboxylic acid, dimethyl ester (IV) (18.97 g, 60.0 mmol) in DMF (250 mL) was added via addition funnel to a solution of thiocarbonyldiimidazole (11.76 g, 60.0 mmol) in DMF (100 mL) over 2.0 h. The reaction was stirred an additional 30 min. $H_2O$ was added slowly resulting in a copious white precipitate. The precipitate was collected on a filter frit washed with $H_2O$, and dried, to afford the compound as a white solid (16.1 g, 75%). mp 163–166° C. $^1$H NMR (DMSO-d$_6$) δ 8.98 (s, 1H), 7.31 (t, 1H, J=7.7 Hz), 7.17 (m, 2H), 7.06 (s, 1H), 4.88 (s, 1H), 3.55 (s, 6H), 2.27 (s, 6H); IR (KBr) 3314, 2122, 2086, 1681, 1654, 1222 cm$^{-1}$; MS (−ESI) 357 (MH$^-$). Anal. Calcd. for $C_{18}H_{18}N_2O_4S.0.5 H_2O$: C, 58.84; H, 5.21; N, 7.63; S, 8.73. Found: C, 58.89; H, 5.04; N, 8.10; S, 8.73.

EXAMPLE 9

4-[3-[[(cyanoimino)mercaptomethyl]amino]phenyl]-1,4-dihydro-2,6-dimethyl-3,5-pyridinedicarboxylic acid, dimethyl ester, sodium salt (II)

Cyanamide (2.52 g, 60 mmol) in EtOH (50 mL) was added to a solution of sodium (1.38 g, 60 mmol) in EtOH (150 mL). The isothiocyanate (Example 8) (17.9 g, 50 mmol) in EtOH (150 mL) was then added to the sodium cyanamide solution via an addition funnel. After the addition was complete, the reaction was brought to a brief boil and then allowed to stir for 1.0 h. at room temperature. The mixture was then concentrated and the residue triturated with EtOAc to provide the compound as a yellow solid (22.6 g, 100%). $^1$H NMR (DMSO-$d_6$) δ 9.05 (s,1H), 7.51 (s,1H), 7.35 (d,1H, J=8.0 Hz), 6.98 (t,1H, J=8.0 Hz), 6.65 (d,1H, J=8.0 Hz), 4.84 (s,1H), 3.57 (s, 6H), 2.27 (s, 6H). $^{13}$C NMR (DMSO-$d_6$) δ 186.5, 167.4, 147.4, 145.7, 140.1, 127.4, 121.2, 119.8, 118.7, 117.6, 101.2, 50.6, 38.0, 18.1; IR (KBr) 2159 cm$^{-1}$.

6. Scheme 2 Intermediates (VI, VII, XIV)

EXAMPLE 10

1,4-Dihydro-2,6-dimethyl-4-[3-[(trifluoroacetyl) amino]phenyl]-3,5-pyridinedicarboxylic acid, dimethyl ester (VI)

A solution of 1,4-dihydro-4-(3-aminophenyl)-2,6-dimethyl-3,5-pyridinedicarboxylic acid, dimethyl ester (IV) (10.0 g, 31.6 mmol) in $CH_2Cl_2$ (500 mL) containing pyridine (2.8 mL, 35 mmol) was cooled to 0° C. Trifluoroacetic anhydride (4.7 mL, 33 mmol) was then added dropwise, and the resulting mixture was stirred at room temperature for 2 h, resulting in a thick suspension. A white solid was collected by filtration and dried in an Abderhalden apparatus for 2 h to afford the compound (9.58 g, 74%). This material was not characterized, but was directly converted to (VII).

EXAMPLE 11

1,4-Dihydro-2,6-dimethyl-4-[3-[methyl (trifluoroacetyl)amino]phenyl]-3,5-pyridinedicarboxylic acid, dimethyl ester (VII)

To a solution of compound (VI) (Example 10) (2.06 g, 5.0 mmol) in DMF (20 mL) under $N_2$ was added NaH (60% mineral oil dispersion, 240 mg, 6.0 mmol). This mixture was stirred for 10 min, followed by the addition of MeI (0.60 mL, 10 mmol). The reaction mixture was stirred for 1h, and then was quenched with $H_2O$ (100 mL). A precipitate readily formed, which was collected by filtration and rinsed with $H_2O$. The resulting solid was taken up in $CH_2Cl_2$, dried ($Na_2SO_4$), and the solvent was removed in vacuo to furnish the compound as a light amber solid (1.91 g, 90%). mp 184–186° C.; MS (ESI) m/z 425 (MH$^+$). $^1$H NMR (DMSO-$d_6$) δ 8.92 (s, 1H), 7.34 (t, 1H, J=7.8 Hz), 7.19 (m, 2H), 7.09 (s, 1H), 4.87 (S, 1H), 3.52 (s, 6H), 3.25 (s, 3H), 2.26 (s, 6H). Anal. Calcd. for $C_{20}H_{21}F_3N_2O_5$.0.2 $H_2O$: C, 55.84; H, 5.02; N, 6.52. Found: C, 55.84; H, 4.96; N, 6.24.

EXAMPLE 12

1,4-Dihydro-2,6-dimethyl-4-[3-(methylamino) phenyl]-3,5-pyridinedicarboxylic acid, dimethyl ester (XIV)

A solution of compound (VII) (Example 11) (1.67 g, 3.92 mmol) in EtOH (30 mL) and 1N NaOH (30 mL) was heated to reflux, and then was cooled and extracted with $CH_2Cl_2$. The organic extract was dried ($Na_2SO_4$), and the solvent was removed in vacuo to afford the compound as a pale yellow solid (1.11 g, 86%). mp 182–184° C.; MS (ESI) m/z 329 (MH$^+$). $^1$H NMR (DMSO-$d_6$) δ 8.78 (s, 1H), 6.91 (t, 1H, J=7.8 Hz), 6.33 (m, 2H), 6.26 (d, 1H, J=8.1 Hz), 5.45 (q, 1H, J=5.1 Hz), 4.82 (s, 1H), 3.56 (s, 6H), 2.60 (d, 3H, J=5.1 Hz), 2.25 (s, 6H).

7. Formula (I) Products

EXAMPLE 13

4-[3-[[(Cyanoimino)[[3-[4-phenyl-1-piperidinyl] propyl]amino]methyl]methylamino]phenyl]-1,4-dihydro-2,6-dimethyl-3,5-pyridinedicarboxylic acid, dimethyl ester (Synthesis via Scheme 2.)

To a solution of N-cyano-N'-[3-(4-phenyl-1-piperidinyl) propyl]isothiourea sodium salt (IX) (115 mg, 0.35 mmol) and the aniline intermediate (XIV) from Example 12 (115 mg, 0.35 mmol) in THF (7 mL) at 0° C. was added $HgCl_2$ (95 mg, 0.35 mmol). The reaction mixture was then refluxed for 3 h. After cooling to room temperature, $H_2O$ (1 mL) was added, and the mixture was stirred for 30 min. A gray precipitate was collected by filtration, and rinsed with $CH_2Cl_2$, the organic extract was dried ($Na_2SO_4$), and the solvent was removed in vacuo. The residue was subjected twice to flash chromatography (silica gel, MeOH:$CH_2Cl_2$, 4:96) to afford the compound as a white solid (15 mg, 4.5%). mp 85–90° C.; MS (ESI) m/z 599 (MH$^+$); $^1$H NMR (CDCl$_3$) δ 7.30 (m, 8 h), 6.98 (d, 1H, J=7.8 Hz), 6.91 (s, 1H), 5.29 (br s, 1H), 5.09 (s, 1 H), 3.67 (s, 6H), 3.63 (m, 2H), 3.47 (m, 2H), 3.37 (s, 3H), 3.00 (m, 2H), 2.73 (m, 4H), 2.45 (s, 6H), 2.38 (m, 1H), 2.26 (m, 2H), 2.03 (m, 2H); $^{13}$C NMR (CDCl$_3$) δ 168.2, 150.4, 146.8, 130.6, 129.0, 128.0, 127.4, 127.0, 124.9, 124.1, 117.3, 102.3, 54.1, 51.4, 51.3, 40.8, 40.3, 39.9, 38.9, 30.4, 25.4, 19.3. HRMS (FAB) Calcd. for $C_{34}H_{43}N_6O_4$ (MH$^+$): m/z 599.3346. Found: 599.3362.

EXAMPLE 14

General Procedure for the Scheme 1 Synthesis of Formula (I) Products

Under a $N_2$ atmosphere, $HgCl_2$ (0.27 g, 1.0 mmol) was added to a cooled (0° C.) suspension of the dihydropyridine aniline derivative (IV) (1.0 mmol), and a diamine (V) (1.5 mmol) in THF (25 mL). The reaction mixture was stirred for 3 h while warming to room temperature. The reaction was then quenched with $H_2O$ (0.2 mL), and was stirred overnight. The resulting black precipitate was removed by vacuum filtration over Celite, and $CH_2Cl_2$ (25 mL) was added to the filtrate. This solution was extracted twice with 1N NaOH (25 mL), the organic extract was dried ($Na_2SO_4$), and the solvent was removed in vacuo. The crude product was generally flash chromatographed, over silica gel with the indicated eluent, to afford the target Formula (I) compound. By this method, the following Formula (I) products were prepared.

EXAMPLE 15

4-[3-[[(Cyanoimino)[[2-[4-(3-methoxyphenyl)-1-piperidinyl]ethyl]amino]methyl]amino]phenyl]-1,4-dihydro-2,6-dimethyl-3,5-pyridinedicarboxylic acid, dimethyl ester The compound was isolated as a beige solid (33%) after purification by flash chromatography ($CH_2Cl_2$:MeOH, 99:1). mp 116–121° C. $^1$H NMR (DMSO-$d_6$) δ 8.92 (s, 1H), 7.18–7.10 (m, 3H), 6.92 (d, 2H, J=7.6 Hz), 6.83–6.74 (m, 3H), 4.90 (s, 1H), 3.74 (s, 3H), 3.52 (s, 6H), 3.34 (s, 6H), 3.00 (d, 2H, J=10.5 Hz), 2.26 (s, 6H), 2.09 (t, 2H, J=11.4 Hz), 1.74–1.56 (m, 3H); $^{13}$C NMR (DMSO-$d_6$) δ 167.3, 159.3, 158.5, 148.6, 147.8, 146.0, 137.6, 129.3, 128.4, 123.2, 121.9, 120.8, 118.8, 117.4, 112.5, 111.4, 101.2, 56.9, 54.8, 53.5, 50.7, 41.7, 39.2, 38.3, 32.8, 18.2. HRMS Calcd. for $C_{33}H_{41}N_6O_5(MH^+)$: 601.3139 Found: 601.3147.

EXAMPLE 16

4-[3-[[(Cyanoimino)[[4-[4-(3-methoxyphenyl)-1-piperidinyl]butyl]amino]methyl]amino]phenyl]-1,4-dihydro-2,6-dimethyl-3,5-pyridinedicarboxylic acid, dimethyl ester hydrate The compound was isolated as a yellow oil (32%) after purification by flash chromatography ($CH_2Cl_2$:MeOH, 99:1). $^1H$ NMR (DMSO-$d_6$) δ 8.91 (d, 2H, J=8.0 Hz); 7.25–7.14 (m, 3H), 7.04 (s, 1H), 6.98 (d, 1H, J=7.9 Hz), 6.90 (d, 1H, J=7.7 Hz), 6.80–6.74 (m, 3H), 4.89 (s, 1H), 3.80 (s, 3H), 3.56 (s, 6H), 3.34 (s, 8H), 3.22 (d, 2H, J=5.5 Hz), 3.04 (bs, 2H), 2.27 (s, 6H), 1.74 (m, 3H), 1.51 (bs, 2H); $^{13}C$ NMR (DMSO-$d_6$) δ 167.3, 159.3, 157.9, 148.5, 145.9, 137.6, 129.3, 128.4, 123.1, 121.7, 120.7, 118.8, 117.3, 112.4, 111.4, 101.1, 89.3, 54.9, 53.5, 50.7, 41.3, 38.3, 26.8, 18.2. Anal. Calcd for $C_{35}H_{44}N_6O_5.1.6 H_2O$: C, 63.93; H, 7.24; N, 12.78. Found: C, 63.82; H, 6.99; N, 12.84.

EXAMPLE 17

4-[3-[[(Cyanoimino)[[3-(4-phenyl-1-piperidinyl)propyl]amino]methyl]amino]phenyl]-1,4-dihydro-2,6-dimethyl-3,5-pyridinedicarboxylic acid, dimethyl ester hydrate The compound was isolated as an airy off-white solid (72%) after purification by flash chromatography ($CH_2Cl_2$:MeOH, 99:1). mp 131–135° C. Anal. Calcd for $C_{33}H_{40}N_6O_4.1.0 H_2O$: C, 65.76; H, 7.02; N, 13.94 Found: C, 65.59; H, 6.91; N, 13.84.

EXAMPLE 18

4-[3-[[(Cyanoimino)[[3-[4-(3-methoxyphenyl)-1-piperidinyl]propyl]amino]methyl]amino]phenyl]-1,4-dihydro-2,6-dimethyl-3,5-pyridinedicarboxylic acid, dimethyl ester, hydrochloride salt, dihydrate The compound was isolated as an ivory solid (58%) after purification by flash chromatography ($CH_2Cl_2$:MeOH, 20:1). The product was characterized as the HCl salt: mp 135° C. Anal. Calcd for $C_{34}H_{42}N_6O_5.HCl.2.0 H_2O$: C, 59.44; H, 6.89; N, 12.27. Found: C, 59.33; H, 6.47; N, 12.05.

EXAMPLE 19

4-[3-[[(Cyanoimino)[[3-[4-cyclohexyl-1-piperidinyl]propyl]amino]methyl]amino]phenyl]-1,4-dihydro-2,6-dimethyl-3,5-pyridinedicarboxylic acid, dimethyl ester, hemihydrate The compound was isolated as a yellow solid (47%) after purification by flash chromatography ($CH_2Cl_2$:MeOH, 6:1). The product was characterized as the HCl salt: mp 171–178° C. Anal. Calcd for $C_{33}H_{46}N_6O_4.HCl.1.5H_2O$: C, 60.58; H, 7.70; N, 12.85. Found: C, 60.38; H, 7.34; N, 12.70.

EXAMPLE 20

4-[3-[[(Cyanoimino)[[3-[4-phenyl-1-piperidinyl]propyl]methylamino]methyl]amino]phenyl]-1,4-dihydro-2,6-dimethyl-3,5-pyridinedicarboxylic acid, dimethyl ester The crude product was taken up in $CH_2Cl_2$, from which a precipitate formed. Filtration afforded the product as a light amber solid (30%): mp 135–145° C. (sintered); MS (ESI) m/z 599 (MH$^+$); IR (KBr) 2181 cm$^{-1}$. Anal. Calcd. for $C_{34}H_{42}N_6O_4.0.6 CH_2Cl_2$: C, 63.97; H, 6.70; N, 12.94. Found: C, 63.93; H, 6.48; N, 13.11.

EXAMPLE 21

4-[3-[[(Cyanoimino)[[3-[4-phenyl-1-piperidinyl]propyl]methylamino]methyl]amino]-4-fluorophenyl]-1,4-dihydro-2,6-dimethyl-3,5-pyridinedicarboxylic acid, dimethyl ester Following the schemes and procedures described supra, 4-fluoro-3-nitrobenzaldehyde was carried through to 1,4-dihydro-4-[(4-fluoro-3- isothiocyanato)phenyl]-2,6-dimethyl-3,5-pyridine dicarboxylic acid, dimethyl ester and then converted into the corresponding N-cyanoisothiourea salt by treatment with an equivalent amount of sodium cyanamide in EtOH. The salt was not purified, but was dried and used in the subsequent $HgCl_2$ mediated coupling with intermediate (V) to produce the title compound (I) which was isolated as a dried foam (150 mg, 47%) after flash column chromatography (silica gel, $CH_2Cl_2$:MeOH, 10:1). $^1H$ NMR (CDCl$_3$) δ 7.45 (br. s, 1H), 7.24 (m, 1H), 7.18 (m, 1H), 7.15–7.05 (m, 5H), 6.95 (t, 1H, J=9.3Hz), 6.19 (br. 2H), 4.97 (s,1H), 3.60 (s, 6H), 3.46 (m, 2H), 3.00–2.96 (m, 3H), 2.52 (m, 4H), 2.34 (s, 6H), 2.04 (m, 3H), 1.82–1.69 (m, 4H), 1.51 (m, 2H). Anal. Calcd. for $C_{33}H_{39}F_1N_6O_4.1.4 H_2O$: C, 63.12; H, 6.71; N, 13.38. Found: C, 63.46; H, 6.52; N, 12.94.

EXAMPLE 22

4-[3-[[(Cyanoimino)[[3-[4-(3-methoxyphenyl)-1-piperidinyl]propyl]methylamino]methyl]amino]-4-fluorophenyl]-1,4-dihydro-2,6-dimethyl-3,5-pyridinedicarboxylic acid, dimethyl ester Following the same procedure as for Example 21, the cyanoisothiourea salt was converted into the desired product (I) via coupling with the appropriate diamine (V). The compound was isolated as a dried foam (52%) after flash column chromatography (silica gel, $CH_2Cl_2$:MeOH, 10:1): $^1H$ NMR (CDCl$_3$) δ 7.36 (br. s, 1H), 7.2–6.8 (m, 5H), 6.7–6.5 (m, 3H), 6.4 (br. s 1H), 4.97 (s, 1H), 3.79 (s, 3H), 3.63 (s, 6H), 3.45 (m, 2H), 2.97–2.93 (m, 2H), 2.48 (m, 2H), 2.34 (s, 6H), 2.0 (m, 2H), 1.6–1.8 (m, 5H), 1.6–1.4 (m, 2H). Anal. Calcd. for $C_{34}H_{42}F_1N_6O_5.0.75H_2O$: C, 63.19; H, 6.63; N, 13.01. Found: C, 62.82; H, 6.37; N, 13.42.

A number of additional Formula (I) compounds were prepared using combinatorial, parallel synthesis chemical techniques. Intermediates of Formula (II) the sodium N-cyanoisothiourea salts, could be stored and reacted in a combinatorial fashion with various Formula (V) diamines and mercuric chloride to provide Formula (I) products.

EXAMPLE 23

General Procedure for Combinatorial Synthesis of Formula (I) Products

Simultaneous reactions were performed using 19 diamines (V). A diamine (V) (0.20 mmol), the sodium N-cyanoisothiourea salt (II) (0.30 mmol) and $HgCl_2$ (0.082 g, 0.30 mmol) were placed into individual 15 mL reaction vials equipped with a stir bar. THF (4 mL) was added to each vial. The vials were closed with Teflon lined screw caps and the resulting suspensions were stirred at room temperature for 1 h. The reaction mixtures were vacuum filtered through 8 mL Bond Elut cartridges containing Celite. A Varian Vac Elut SPS 24 was used and each effluent was collected in a 16×100 mm test tube. THF (2 mL) was used to complete the transfer to the Celite bed. An aliquot (0.05 mL) of each THF effluent was diluted in MeOH (0.2 mL) and analyzed by analytical HPLC and LC-MS. The remainder of each THF effluent was evaporated using a Savant Speed Vac. Samples that were ≧80% pure by HPLC were not further purified by preparative HPLC. To remove any residual $HgCl_2$, such samples were partitioned between EtOAc (4 mL) and $H_2O$ (3×2 mL) and then the organic layer was evaporated to give the Formula (I) products. Samples ≦80% pure by HPLC were subjected to automated preparative HPLC. The MeOH portion of the fractions was evaporated using the Speed Vac. The resulting aq. solutions were treated with aq. $Na_2CO_3$ (0.7 mL, 2 M) and then extracted with EtOAc (8 mL). The organic layers were washed with aq. $Na_2CO_3$ (2.7 mL, 0.5 M) and then $H_2O$ (3×2 mL). Two aliquots (0.05 mL each) of these organic solutions were removed for final product HPLC and MS analysis. The remainder of the organic solutions were then transferred to tared 16×100 mm test tubes and evaporated using the Speed Vac to give the product.

As can be seen, the desired Formula (I) product may be obtained by appropriate selection of Formula (IV) and (V) starting materials (e.g. Scheme 1) or Formula (XIV) and (IX) starting materials (e.g. Scheme 2). Other modifications of reactants and procedures to produce these products would be known to one skilled in the art of organic chemical synthesis.

Some additional examples of Formula (I) products are contained in Tables 1, 2 and 3.

TABLE 1

Formula (I) Products
Z is Piperidine

($R^1$—$R^4$ = Me)

| Ex. | $R_{10}$ | n | Y | $R^9$ | % Yield | Mol. Formula | Mp° C. | M/Z MH+ |
|---|---|---|---|---|---|---|---|---|
| 24 | H | 3 | H | $CH_2Ph$ | 53 | $C_{34}H_{41}N_6O_4$ | indistinct | 597 |
| 25 | H | 2 | H | Ph | 62 | $C_{34}H_{42}N_8O_4$ | 160–165 | — |
| 26 | H | 4 | H | Ph | 54 | $C_{32}H_{38}N_6O_4$ | 100–105 | — |
| 27 | H | 3 | H | 2-MeOPh | 56 | $C_{38}H_{46}N_6O_9$ | indistinct | — |
| 28 | H | 3 | H | 3-HOPh | 36 | $C_{33}H_{40}N_6O_5$ | 115–120 | — |
| 29 | H | 3 | H | 4-FPh | 39 | $C_{33}H_{39}FN_6O_4$ | 105–110 | — |
| 30 | H | 3 | H | 1-naphthyl | 66 | $C_{37}H_{43}N_6O_4$ | — | 635 |
| 31 | H | 3 | H | 3-$Me_2$NPh | 73 | $C_{35}H_{45}N_7O_4$ | 110–115 | — |
| 32 | H | 3 | OH | 4-MePh | 60 | $C_{34}H_{42}N_6O_5$ | 143–155 | — |
| 33 | H | 3 | OH | 4-FPh | 49 | $C_{33}H_{39}FN_6O_5$ | 118–128 | — |
| 34 | H | 3 | $CO_2Me$ | Ph | 31 | $C_{35}H_{42}N_6O_6$ | — | 643 |
| 35 | H | 3 | CN | Ph | 46 | $CC_{34}H_{39}N_7O_4$ | — | 608 |
| 36 | 4-F | 3 | $CO_2Me$ | Ph | 42 | $C_{35}H_{41}FN_6O_6$ | — | 661 |
| 37 | 4-F | 3 | CN | Ph | 58 | $C_{34}H_{38}FN_7O_4$ | — | 628 |
| 38 | 4-F | 3 | H | t-Bu | 68 | $C_{31}H_{43}FN_6O_4$ | — | — |
| 39 | H | 3 | H | 3-IPh | 38 | $C_{33}H_{39}IN_6O_4$ | — | — |
| 40 | H | 3 | H | H | 50 | $C_{37}H_{36}N_6O_4$ | — | 509 |
| 41 | H | 3 | H | Me | 41 | $C_{28}H_{38}N_6O_4$ | — | 523 |
| 42 | H | 3 | H | Et | 53 | $C_{29}H_{40}N_6O_4$ | — | 537 |
| 43 | H | 3 | H | Pr | 77 | $C_{30}H_{42}N_6O_4$ | — | 551 |
| 44 | H | 3 | H | i-Pr | 21 | $C_{30}H_{42}N_6O_4$ | — | 551 |
| 45 | H | 3 | H | $NMe_2$ | 4 | $C_{29}H_{41}N_7O_4$ | — | 552 |
| 46 | H | 3 | H | t-Bu | 24 | $C_{31}H_{44}N_6O_4$ | — | 565 |
| 47 | H | 3 | H | $CH_2NMe_2$ | 33 | $C_{30}H_{43}N_7O_4$ | — | 566 |
| 48 | H | 3 | H | pyrrolidinyl | 23 | $C_{31}H_{43}N_7O_4$ | — | 578 |
| 49 | H | 3 | H | $CH_2CH_2NMe$ | 18 | $C_{31}H_{45}N_7O_4$ | — | 580 |

TABLE 1-continued
Formula (I) Products
Z is Piperidine
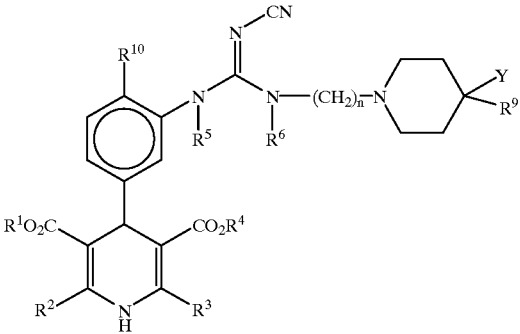
(R¹—R⁴ = Me)
| Ex. | $R_{10}$ | n | Y | $R^9$ | % Yield | Mol. Formula | Mp° C. | M/Z MH⁺ |
|---|---|---|---|---|---|---|---|---|
| 50 | H | 3 | H |  | 23 | $C_{32}H_{45}N_7O_4$ | — | 592 |
| 51 | H | 3 | H | 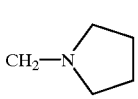 | 35 | $C_{32}H_{45}N_7O_4$ | — | 592 |
| 52 | H | 3 | H |  | 23 | $C_{31}H_{43}N_7O_5$ | — | 594 |
| 53 | H | 3 | H | 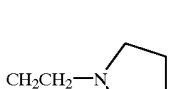 | 32 | $C_{33}H_{47}N_7O_4$ | — | 606 |
| 54 | H | 3 | H | 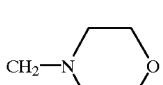 | 34 | $C_{32}H_{45}N_7O_5$ | — | 608 |
| 55 | H | 3 | H | 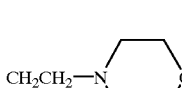 | 44 | $C_{33}H_{47}N_7O_5$ | — | 622 |

TABLE 2

Formula (I) Products
Z is Tetrahydropyridine ($R^1$—$R^4$ = Me)

| Ex. | $R^{10}$ | n | $R^9$ | % Yield | Mol. Formula | Mp ° C. | M/Z MH$^+$ |
|---|---|---|---|---|---|---|---|
| 56 | H | 3 | 4-MePh | 45 | $C_{34}H_{41}N_6O_4$ | 114–124 | 597 |
| 57 | H | 3 | 4-FPh | 53 | $C_{33}H_{37}FN_6O_4$ | — | — |
| 58 | H | 3 | 1-naphthyl | 11 | $C_{37}H_{40}O_6O_4$ | — | 633 |

TABLE 3

Formula (I) Products
Z is Piperazine ($R^1$—$R^4$ = Me)

| Ex. | $R^{10}$ | n | $R^9$ | % Yield | Mol. Formula | Mp ° C. | M/Z MH$^+$ |
|---|---|---|---|---|---|---|---|
| 59 | H | 3 | c-hexyl | 39 | $C_{32}H_{45}N_7O_4$ | — | 592 |
| 60 | H | 3 | Et | 60 | $C_{28}H_{39}N_7O_4$ | 127–132 | — |
| 61 | H | 3 | n-Pr | 86 | $C_{29}H_{41}N_7O_4$ | 115–120 | — |
| 62 | H | 3 | i-Pr | 85 | $C_{29}H_{41}N_7O_4$ | 145–150 | — |
| 63 | H | 3 | c-Pr | 42 | $C_{29}H_{39}N_7O_4$ | 115–120 | — |
| 64 | H | 3 | n-Bu | 92 | $C_{30}H_{43}N_7O_4$ | 135–140 | — |
| 65 | H | 3 | i-Bu | 97 | $C_{30}H_{44}N_7O_4$ | 155–160 | 566 |
| 66 | H | 3 | t-Bu | 33 | $C_{30}H_{43}N_7O_4$ | 110–115 | — |
| 67 | H | 3 | $CH_2$c-Pr | 93 | $C_{30}H_{41}N_7O_4$ | 145–150 | — |
| 68 | H | 3 | c-pentyl | 97 | $C_{31}H_{43}N_7O_4$ | 150–155 | — |
| 69 | H | 3 | $CO_2$t-Bu | 79 | $C_{31}H_{43}N_7O_6$ | 115–120 | — |
| 70 | H | 3 | Ph | 69 | $C_{32}H_{40}N_7O_4$ | 90–95 | 586 |
| 71 | H | 3 | 4-FPh | 80 | $C_{32}H_{39}N_7O_4$ | 95–100 | 604 |
| 72 | H | 3 | 3-MeOPh | 82 | $C_{33}H_{42}N_7O_5$ | 110–115 | 616 |
| 73 | H | 3 | 3-Me2NPh | 54 | $C_{34}H_{44}N_8O_4$ | 130–140 | — |
| 74 | H | 3 | 3-HOPh | 40 | $C_{32}H_{39}N_7O_5$ | 110–120 | — |
| 75 | 4-F | 3 | c-hexyl | 56 | $C_{32}H_{44}N_7O_4$ | — | — |
| 76 | H | 3 | H | 59 | $C_{26}H_{35}N_7O_4$ | 105–110 | — |

Scheme 1
General Processes for Compound (I) Synthesis
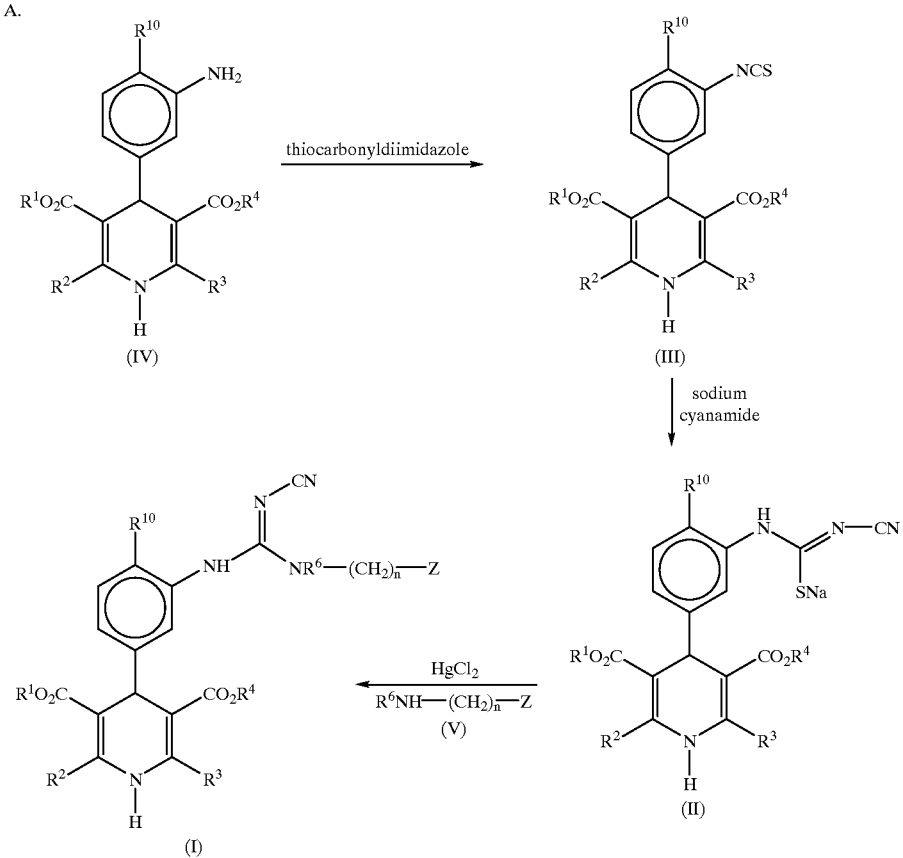
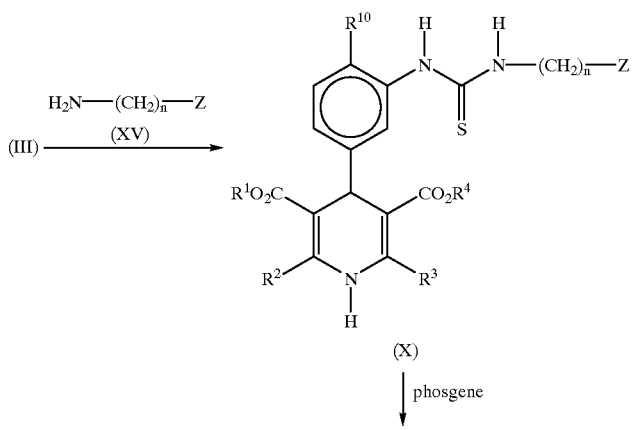

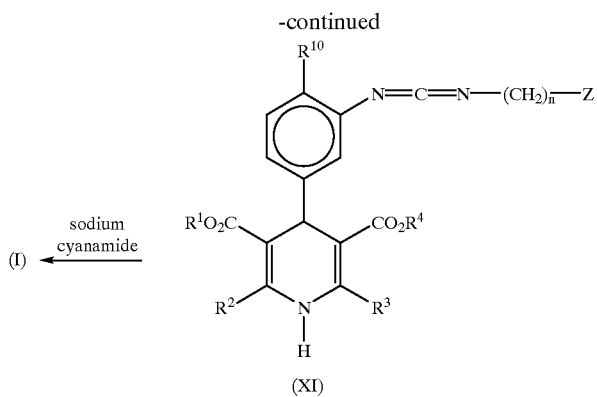
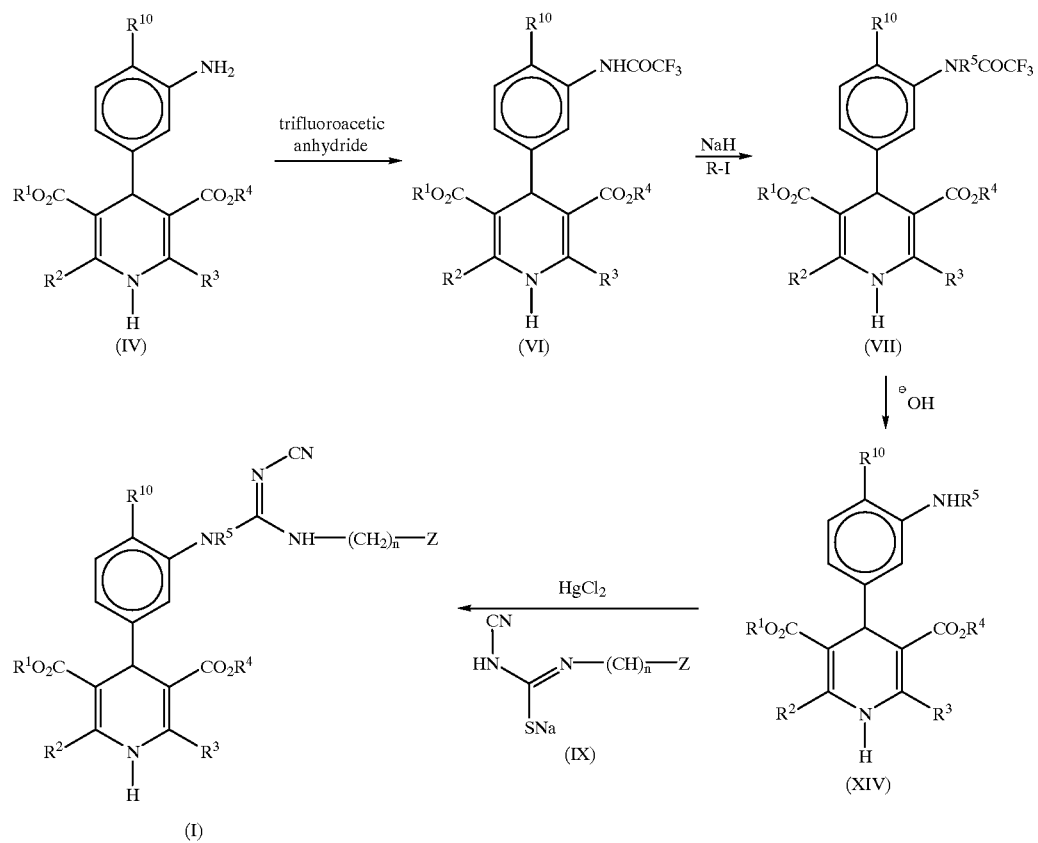

We claim:

1. A compound of Formula (I) and its pharmaceutically acceptable acid addition salts or hydrates thereof

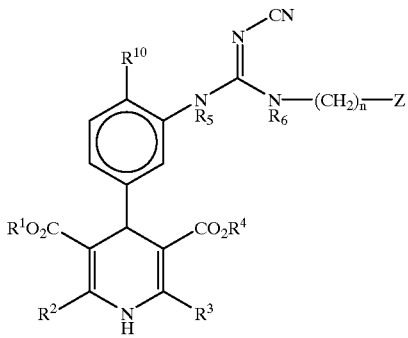 (I)

wherein $R^1$ to $R^4$ are independently selected from lower alkyl;

$R^5$ and $R^6$ are independently selected from hydrogen and lower alkyl;

n is an integer selected from 2 to 5;

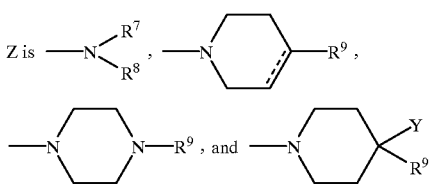

in which $R^7$ and $R^8$ are independently selected from lower alkyl and lower alkanol; the solid and broken line denote a single or double covalent bond; $R^9$ is selected from hydrogen, lower alkyl, —$CO_2R^1$, —$(CH_2)_mX$, and —$(CH_2)_nNR^{11}R^{12}$, wherein wherein m is zero or an integer from 1 to 3 and X is $C_{3-7}$ cycloalkyl, naphthyl, and

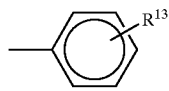

with $R^{13}$ being lower alkyl, lower alkenyl, lower alkoxy, hydrogen, halogen, hydroxy and dialkylamino, and $R^{11}$ and $R^{12}$ are lower alkyl or are taken together as a $C_{3-5}$ alkylene chain or an ethyl-oxy-ethyl chain; and Y is hydrogen, hydroxy, cyano, and —$CO_2Me$; and $R^{10}$ is hydrogen or halogen.

2. A compound of claim 1 wherein Z is

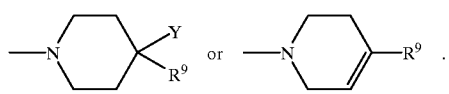

3. A compound of claim 1 wherein Z is

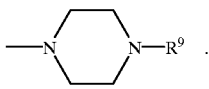

4. A compound of claim 1 wherein $R^9$ is

5. A compound of claim 2 selected from

4-[3-[[(cyanoimino)[[2-[4-(3-methoxyphenyl)-1-piperidinyl]ethyl]amino]methyl]amino]phenyl]-1,4-dihydro-2,6-dimethyl-3,5-pyridinedicarboxylic acid, dimethyl ester;

4-[3-[[(cyanoimino)[[4-[4-(3-methoxyphenyl)-1-piperidinyl]butyl]amino]methyl]amino]phenyl]-1,4-dihydro-2,6-dimethyl-3,5-pyridinedicarboxylic acid, dimethyl ester;

4-[3-[[(cyanoimino)[[3-(4-phenyl-1-piperidinyl)propyl]amino]methyl]amino]phenyl]-1,4-dihydro-2,6-dimethyl-3,5-pyridinedicarboxylic acid, dimethyl ester;

4-[3-[[(cyanoimino)[[3-[4-(3-methoxyphenyl)-1-piperidinyl]propyl]amino]methyl]amino]phenyl]-1,4-dihydro-2,6-dimethyl-3,5-pyridinedicarboxylic acid, dimethyl ester;

4-[3-[[(cyanoimino)[[3-[4-(2-methoxyphenyl)-1-piperidinyl]propyl]amino]methyl]amino]phenyl]-1,4-dihydro-2,6-dimethyl-3,5-pyridinedicarboxylic acid, dimethyl ester, maleic acid salt, hydrate;

4-[3-[[(cyanoimino)[[3-[4-(3-hydroxyphenyl)-1-piperidinyl]propyl]amino]methyl]amino]1,4-dihydro-2,6-dimethyl-3,5-pyridinedicarboxylic acid, dimethyl ester maleic acid salt;

4-[3-[[(cyanoimino)[[3-[[(4-(fluorophenyl)-1-piperidinyl]propyl]amino]methyl]amino]phenyl]-1,4-dihydro-2,6-dimethyl-3,5-pyridinedicarboxylic acid, dimethyl ester, hydrate;

4-[3-[[(cyanoimino)[[3-[4-(1-naphthalenyl)-1-piperidinyl]propyl]amino]methyl]amino]phenyl]-1,4-dihydro-2,6-dimethyl-3,5-pyridinedicarboxylic acid, dimethyl ester maleate;

4-[3-[[(cyanoimino)[[3-[4-[3-(dimethylamino)phenyl]-1-piperidinyl]propyl]amino]methyl]amino]phenyl]-1,4-dihydro-2,6-dimethyl-3,5-pyridinedicarboxylic acid, dimethyl ester;

4-[3-[[(cyanoimino)[[3-[4-(4-fluorophenyl)-4-hydroxy-1-piperidinyl]propyl]amino]methyl]amino]phenyl]-1,4-dihydro-2,6-dimethyl-3,5-pyridinedicarboxylic acid, dimethyl ester, hydrate;

4-[3-[[(cyanoimino)[[3-(4-methoxycarbonyl)-4-phenyl-1-piperidinyl)propyl]amino]methyl]amino]phenyl]-1,4-dihydro-2,6-dimethyl-3,5-pyridinedicarboxylic acid, dimethyl ester;

1,4-dihydro-4-[3-iodo-5-[[[[3-[4-phenyl-1-piperidinyl]propyl]amino]cyano(iminomethyl)]amino]phenyl]-2,6-dimethyl-3,5-pyridinedicarboxylic acid, dimethyl ester;

4-[3-[[(cyanoimino)[[3-[1,2,3,6-tetrahydro-4-(4-fluorophenyl)-1-piperidinyl]-propyl]amino]methyl]amino]phenyl]-1,4-dihydro-2,6-dimethyl-3,5-pyridinedicarboxylic acid, dimethyl ester, maleic acid salt;

4-[3-[[(cyanoimino)[[3-[4-phenyl-1-piperidinyl]propyl]methylamino]methyl]amino]-4-fluorophenyl]-1,4- dihydro-2,6-dimethyl-3,5-pyridinedicarboxylic acid, dimethyl ester;

4-[3-[[(cyanoimino)[[3-[4-(3-methoxyphenyl)-1-piperidinyl]propyl]methylamino]methyl]amino]-4-fluorophenyl]-1,4-dihydro-2,6-dimethyl-3,5-pyridinedicarboxylic acid, dimethyl ester;

4-[3-[[(cyanoimino)[[3-(4-methyl-1-piperidinyl)propyl]amino]methyl]amino]phenyl]-1,4-dihydro-2,6-dimethyl-3,5-pyridinedicarboxylic acid, dimethyl ester;

4-[3-[[(cyanoimino)[[3-(4-ethyl-1-piperidinyl)propyl]amino]methyl]amino]phenyl]-1,4-dihydro-2,6-dimethyl-3,5-pyridinedicarboxylic acid, dimethyl ester;

4-[3-[[(cyanoimino)[[3-(4-propyl-1-piperidinyl)propyl]amino]methyl]amino]phenyl]-1,4-dihydro-2,6-dimethyl-3,5-pyridinedicarboxylic acid, dimethyl ester;

4-[3-[[(cyanoimino)[[3-[4-(methylethyl)-1-piperidinyl]propyl]amino]methyl]amino]phenyl]-1,4-dihydro-2,6-dimethyl-3,5-pyridinedicarboxylic acid, dimethyl ester; and 4-[3-[[(cyanoimino)[[3-[4-(1,1-dimethylethyl)-1-piperidinyl]propyl]amino]methyl]amino]phenyl]-1,4-dihydro-2,6-dimethyl-3,5-pyridinedicarboxylic acid, dimethyl ester.

6. A compound of claim 3 selected from

4-[3-[[(cyanoimino)[[3-(4-cyclopentyl-1-piperazinyl)propyl]amino]methyl]amino]phenyl]-1,4-dihydro-2,6-dimethyl-3,5-pyridinedicarboxylic acid, dimethyl ester dimaleate;

4-[3-[[(cyanoimino)[[[3-[4-(1,1-dimethylethyoxy)carbonyl]-1-piperazinyl]propyl]amino]methyl]amino]phenyl]-1,4-dihydro-2,6-dimethyl-3,5-pyridinedicarboxylic acid, dimethyl ester;

4-[3-[[(cyanoimino)[[3-(4-phenyl-1-piperazinyl)propyl]amino]methyl]amino]phenyl]-1,4-dihydro-2,6-dimethyl-3,5-pyridinedicarboxylic acid, dimethyl ester;

4-[3-[[(cyanoimino)[[3-[4-(4-fluorophenyl)-1-piperazinyl]propyl]amino]methyl]amino]phenyl]-1,4-dihydro-2,6-dimethyl-3,5-pyridinedicarboxylic acid, dimethyl ester; and 4-[3-[[(cyanoimino)[[3-[4-(3-methoxyphenyl)-1-piperazinyl]propyl]amino]methyl]amino]phenyl]-1,4-dihydro-2,6-dimethyl-3,5-pyridinedicarboxylic acid, dimethyl ester.

7. A pharmaceutical composition for use in promoting weight loss and treating eating disorders, the composition comprising an anorexiant effective amount of a compound claimed in claim 1 in combination with a pharmaceutically acceptable carrier.

8. A method of promoting weight loss and treating eating disorders in a mammal which comprises administering to a mammalian host an anorexiant effective dose of a compound claimed in claim 1.

* * * * *